United States Patent [19]

von Schulthess et al.

[11] 4,164,558

[45] Aug. 14, 1979

[54] METHOD FOR OPTIMIZING REAGENTS FOR AGGLUTINATION REACTIONS

[75] Inventors: Gustav K. von Schulthess; Richard J. Cohen, both of Brookline; George B. Benedek, Belmont, all of Mass.

[73] Assignee: Massachusetts Institute of Technology, Cambridge, Mass.

[21] Appl. No.: 743,678

[22] Filed: Nov. 22, 1976

[51] Int. Cl.² .................... G01N 31/00; G01N 33/16
[52] U.S. Cl. ................................... 424/12; 23/230 B; 424/8; 424/11; 424/13; 435/7
[58] Field of Search ........... 23/230 R, 230 B, 253 TP; 424/3, 7, 8, 11, 12, 13; 195/103.5 A

[56] References Cited

PUBLICATIONS von Schulthess et al., Immunochem., vol. 13, No. 12, 1976, pp. 955-962 (published Jan. 12, 1977).
Oreskes, J. Immunology, vol. 86, 1961, pp. 338-343.
Van Oss, Res-J. Soc. Retic. Soc., vol. 3, 1966, pp. 29-40.
Sobers, Bayou Tech., La. State Soc. Med. Tech., vol. XVII, May, 1973, pp. 18-20, 22.

*Primary Examiner*—Anna P. Fagelson
*Attorney, Agent, or Firm*—Arthur A. Smith, Jr.; Paul J. Cook

[57] ABSTRACT

A method and compositions are provided to effect optimization of methods for determining concentrations of antibodies or antigens. Particles coated with an antigen or an antibody are suspended in an aqueous medium where pH and ionic strength are controlled so that the coulomb effect and the van der Waals forces on and exerted by the particles are balanced.

6 Claims, No Drawings

METHOD FOR OPTIMIZING REAGENTS FOR AGGLUTINATION REACTIONS

The Government has rights in this invention pursuant to Grant No. NIH-5-P01-HL 14322-04 awarded by the National Institutes of Health and Grant No. DMR 72-03027 A05 and IPA-0010 awarded by the National Science Foundation.

BACKGROUND OF THE INVENTION

This invention relates to a process for making reagents used in the conduction of agglutination reactions. More particularly this invention relates to a process for forming such reagents useful in a process for accurately measuring the concentration of agents that promote or inhibit agglutination reactions, and wherein the extent of the agglutination reaction is determined by quasi-elastic light scattering spectroscopy or other optical methods.

Agglutination reactions are widely used in biology and medicine to detect small quantities of antibody or antigen molecules. Agglutination reactions usually involve the in vitro aggregation of microscopic carrier particles which bear on their surface antigenic molecules. Aggregation occurs when antibody molecules specifically corresponding to the antigen are introduced into the solution of the carrier particles. The converse procedure of agglutinating antibody-coated particles with the appropriate polyhaptenic antigen molecules is also used. Some of the carrier particles which have been used are red blood cells, bacteria and polystyrene spheres. At low concentrations of the agglutination-inducing antibody or antigen (henceforth termed the agglutinator), small aggregates consisting of only a few carrier particles are formed. At higher concentrations of agglutinator the aggregates grow so large as to form visible clumps.

Conventionally, the appearance of this visible agglutinate has been taken as the criterion for the presence of the agglutinator. Clearly, this detection criterion suffers from several defects. First, the formation of the grossly visible agglutinate requires a much larger concentration of agglutinator than needed to form small microscopic aggregates. Moreover, whereas the reversible formation of small aggregates is a specific and reproducible process, the appearance of macroscopic agglutinates is subject to many poorly controlled influences, such as the presence of foreign surfaces. In addition, the appearance of a grossly visible agglutinate is so qualitative a criterion that it is difficult experimentally to determine quantitatively the associated agglutinator concentration. Conventionally, the agglutinator concentration is determined by preparing a serial dilution of the agglutinator-containing solution. Then an aliquot of each dilution is mixed with a fixed amount of carrier particles (henceforth all the reagents, including carrier particles, used in fixed amount will be collectively termed the agglutinant) and the highest degree of dilution which still permits the formation of a visible agglutinate, is noted. This serves to indicate the concentration of agglutinator in the original solution. The agglutinator concentration can at best be determined to within a factor of two by this method.

Thus, while the agglutination reaction, as conventionally performed serves as a specific and versatile means of detecting antigen or antibody molecules, it is severely limited in its application in that: (1) the process is not capable of providing an accurate quantitative measurement of either antigen or antibody concentrations and (2) the process may only be used for determining antibody or antigen concentrations which are sufficiently high so as to induce (or inhibit) macroscopically visible agglutination.

In copending patent application Ser. No. 662,497 filed Mar. 1, 1976 entitled "Immunoassay by Light Scattering Spectroscopy", there is described a process for measuring the concentration of substances capable of promoting or inhibiting agglutination reactions which is substantially more accurate and sensitive than previously known processes used for determining the extent of agglutination reactions.

In the process, the degree of agglutination is determined by measuring the mean diffusion constant $\bar{D}$ of the agglutinated reaction product by means of quasi-elastic light scattering spectroscopy. The measured diffusion constant then is compared with a standard quantitative relationship between the mean diffusion constant of the agglutinated reaction product and the concentration of antigen or antibody being tested. In addition to determining the concentration of antigen or antibody molecules, the process can be used to determine the concentration of any substance capable of specifically promoting or inhibiting an agglutination reaction even when the formation of antigen-antibody bonds is not involved in the agglutination process.

Quasi-elastic light scattering spectroscopy is a laser technique used to study the Brownian motion of particles in solution. The Brownian motion of a particle in solution is characterized by its diffusion constant D, which is a monotonically decreasing function of particle size. This Brownian motion broadens the spectral linewidth of the laser light scattered by the particle in direct proportion to D. The spectrum (or its Fourier transform, the correlation function) of the light scattered from a polydisperse solution of particles is determined by the distribution of diffusion constants of the particles. By analysis of the spectrum (or correlation function) $\bar{D}$ is obtained which is the average of the diffusion constants of the particles weighted by the intensity of the light scattered by each particle. The mean diffusion constant $\bar{D}$ is inversely proportional to the mean hydrodynamic radius of the particles. The appearance of even a few aggregates in a previously monodisperse solution of particles causes a marked drop in $\bar{D}$ because the aggregates scatter light more strongly than do the single particles. The scattered light is measured at a constant angle to the path of incident light. Quasi-elastic light scattering is a particularly suitable means of following agglutination in that it measures only the relative distribution of particle sizes, and is independent of absolute particle concentration. Hence, quasi-elastic scattering measurements are insensitive to the anomalies of precipitation and absorption of particles onto foreign surfaces.

In the process, an agglutination reaction is performed in any of a variety of modes of operation. The agglutination reaction may be used in several different modes to detect antigen or antibody including procedures which utilize carrier particles as follows:

(1) With antigen-coated carrier particles as agglutinant and the complementary antibody as agglutinator.

(2) With antibody-coated carrier particles as agglutinant and the complementary antigen as agglutinator.

(3) The agglutination inhibition mode with antigen-coated spheres wherein a fixed quantity of antibody is mixed with a dilution of the test sample containing the complementary antigen, inactivating a portion of the antibody. This mixture then is combined with the antigen-coated carrier particles. The degree to which the antigen in the test sample inhibits the aggregation of the carrier particles, that would otherwise have occurred, indicates the concentration of antigen present.

(4) The agglutination inhibition mode with antibody-coated spheres wherein a fixed quantity of antigen is mixed with a dilution of the test sample containing the complementary antibody, inactivating a portion of the antigen. This mixture then is combined with the antibody-coated carrier particles. The degree to which the antibody present in the sample inhibits the aggregation of carrier particles, which would otherwise have occurred, indicates the concentration of antibody present.

In modes 1 and 4 the agglutination reaction serves as an antibody assay. In modes 2 and 3 it serves as an antigen assay. Mode 3 is of particular practical importance as an antigen assay since it is generally easier to obtain a sufficient quantity of purified antigen to coat the carrier particles than to obtain a similar quantity of complementary antibody. Moreover, in mode 3 the agglutination reaction serves to detect antigen molecules of any size with one or more haptenic sites. On the other hand, in mode 2 the agglutination reaction serves to detect only polyhaptenic antigens, which are of sufficient size (on the order of 100 Å in diameter) to effect crosslinking of the carrier particles.

A standard quantitative relationship first is established between the mean diffusion constant $\bar{D}$ of the agglutinated reaction product as a function of the concentration of the antigen or antibody being tested for fixed concentrations of the agglutinant composition. Antigen or antibody-coated particles can be prepared by depositing the antigen or antibody of the surface of latex microspheres, red blood cells, bacteria or the like by means well known in the art. In addition, some cells or bacteria naturally bear certain antigens or antibodies on their surface. Serial dilutions of known concentration of the antigen or antibody one wishes to test then are prepared and an agglutination reaction is performed using these serial dilutions of known concentration of antigen or antibody with the fixed concentrations of the agglutinant composition. The concentration of agglutinator present must be sufficiently low so that precipitation of the agglutinated particles does not occur, so that the agglutinated particles remain suspended in solution. The agglutination reaction involves the cross-linking of the coated particles to produce larger particles in proportion to the concentration of active agglutinator present. This crosslinking has the effect of reducing the mean diffusion constant measured by quasi-elastic light scattering spectroscopy in proportion to the concentration of active agglutinator present. For each serial dilution of the known concentration of antigen or antibody tested, each value of $\bar{D}$ is determined for the corresponding agglutinated reaction product by means of quasi-elastic light scattering spectroscopy as described above.

The quantitative relationship so-determined than can be employed as a standard to be applied when performing the agglutination reaction on samples containing unknown amounts of the antigen or antibody being tested. A serial dilution of each sample is prepared. The agglutination reaction is performed using one or several of these dilutions of the sample and the mean diffusion constant $\bar{D}$ is determined. The agglutinant composition employed to establish the standard quantitative relationship must be the same agglutinant composition employed to form the agglutinated reaction product with the antigen or antibody being tested so that an accurate comparison can be made between the standard and the unknown. The measurements of $\bar{D}$ of the agglutinated reaction product obtained with the antigen or antibody being tested are compared with the standard quantitative relationship between $\bar{D}$ and the antigen or antibody concentration, and thus the original concentration of the antigen or antibody in the sample is determined. At least two sample dilutions should be analyzed by light scattering spectroscopy in order to extrapolate the results to the standard quantitative relationship. However, only one sample dilution is needed if it is known that, at the concentration tested, it is within an ascending or descending portion of the relationship between concentration and mean diffusion constant.

It is also possible to use the process to measure the concentration of antigen or antibody without the use of carrier particles. Thus, in addition to the modes of operation set forth above, the concentration of antigen is determined by mixing a fixed amount of complementary antibody to the serial dilutions of the sample which contains the antigen (mode 5). Quasi-elastic light scattering then is used to measure $\bar{D}$ of the reaction product and this is compared with standard quantitative relationship. The larger the antigen-antibody aggregates the smaller is $\bar{D}$. In mode 6 of the method, antibody concentration is determined by mixing a fixed amount of complementary antigen with the serial dilutions of the sample containing the antibody. Once again $\bar{D}$ of the reaction product is measured and is compared with a standard quantitative relationship. In practice, the process is more sensitive in modes 1, 2, 3, 4 where carrier particles are utilized as compared to modes 5 and 6. Also, there is less interference in the measurement of $\bar{D}$ due to light scattered by other elements present in the sample in modes 1, 2, 3, 4 as compared to modes 5 and 6 since the intensity of light scattered by the large carrier particles is generally much greater than that scattered by any other element. However, modes 5 and 6 are useful when it is not possible to bind the antigen or antibody to a suitable carrier particle.

The process provides substantial advantages over the processes of the prior art. Since the process does not require that the agglutination reaction be conducted at such a high concentration of agglutinator and agglutinant that macroscopic precipitation of the agglutination reaction product occurs. Thus, the method can be used to measure much lower antigen or antibody concentrations associated with the microscopic reversible stages of the agglutination reaction. This stage may involve the dimerization of the carrier particles whereas the macroscopically visible agglutinate may contain millions of carrier particles. Moreover, in the process the degree of agglutination is quantitatively measured at the microscopic, reversible and reproducible stage of the agglutination reaction. Thus this process serves to transform the agglutination reaction from a rough qualitative measure of antigen or antibody concentration to an accurate, reproducible means of quantitating antibody or antigen concentrates.

It would be highly desirable to provide a means for optimizing the sensitivity, specificity, accuracy and reproducibility of the immunoassay by light scattering spectroscopy procedure, by optimizing the composition of the reagents used in the procedure. These reagents may comprise antigen, antibody, antigen-coated particles, antibody-coated particles, buffered solvents, various organic and inorganic salts, viruses, red blood cells, bacteria and the like.

SUMMARY OF THE INVENTION

The reagent optimization process disclosed herein may be used to optimize the sensitivity, specificity, accuracy and reproducibility of the process of determining the concentration of agents which promote or inhibit agglutination reactions, wherein the extent of the agglutination reaction is determined by optical means such as by turbidimetric processes or by quasi-elastic light scattering spectroscopy as discussed above. In addition, the process herein disclosed may be used to optimize the sensitivity, specificity, reproducibility and accuracy of the determination of the concentration of agents which promote or inhibit agglutination reactions, by processes which determine the extent of the agglutination reaction by means, including optical means, other than quasi-elastic light scattering spectroscopy. The detection of agents which promote or inhibit agglutination reactions, by such other means for determining the extent of the agglutination reaction, may be carried out in any of the six basic modes of operation discussed above in connection with the quasi-elastic light scattering spectroscopic procedure.

This invention is based upon the fact that in the detection of agents which promote or inhibit agglutination reactions, by processes which involve the determination of the extent of the agglutination reaction, the sensitivity of the detection process is inversely proportional to the concentration of agglutinator needed to achieve a given extent of reaction. This is true for the following reasons: (1) In the direct modes (modes 1, 2, 5 and 6 discussed above) the substance being tested for is itself the agglutinator. Therefore, the sensitivity of the detection process is inversely proportional to the concentration of agglutinator required to achieve a given extent or agglutination reaction (2) In the indirect modes of assay (modes 3 and 4 discussed above) the substance being tested for is used to inactivate a fixed concentration of agglutinator, which, in the absence of the substance being tested for, achieves a given extent of agglutination reaction. The amount of substance being tested for required to inactivate a sufficient fraction of agglutinator to reduce the extent of agglutination a given amount from that which would occur in the absence of the substance being tested for, is in proportion to the concentration of agglutinator required to achieve said extent of reaction.

Therefore, in processes which detect agents which promote or inhibit agglutination reactions, by measuring the extent of agglutination reactions, it is desirable to adjust the reagent composition so that a minimal concentration of agglutinator is required to achieve a given extent of agglutination. The concentration of agglutinator required to achieve a given (low) extent of reaction is inversely proportional to: (1) the number of (antibody or antigen) active agglutinator binding sites present on a carrier particle and (2) the dimerization equilibrium constant defining the interaction of one active agglutinator binding site on a carrier particle with an agglutinator molecule which is already bound to another carrier particle.

In order to maximize the sensitivity, specificity, accuracy and reproducibility of processes which determine the concentration of agents that promote or inhibit agglutination reactions, by measuring the extent of the agglutination reaction, the pH and ionic strengths of the solvent in which the carrier particles are suspended, are adjusted so as to maximize the dimerization equilibrium constant while minimizing nonspecific interactions between carrier particles. The procedure for effecting this result is based upon the recognition that van der Waals attraction forces and coulomb repulsion forces must be balanced in order to avoid nonspecific agglutination while maximizing sensitivity and specificity of the assay. In the procedure, the pH of the solution is regulated as far from the isoelectric point of the antibody or antigen coating material as possible to maximize particle charge without significantly diminishing the specific antigen-antibody binding constant. The ionic strength of the solution then is increased gradually so as to shorten the range of coulomb interaction until nonspecific agglutination occurs as determined by any suitable method such as by the quasi-elastic light scattering process. The ionic strength then is reduced to a value just beyond the value where nonspecific agglutination was observed to occur first.

DESCRIPTION OF SPECIFIC EMBODIMENTS

In order to determine the optimum conditions of pH and ionic strength for the assay, it is useful to consider the nature of the interactions between the coated carrier particles in electrolyte solution. There are three principal interactions involved. The first is the short range van der Waals attraction, which to first approximation is independent of pH and ionic strength. The second interaction is the repulsive coulomb force. The magnitude of this interaction is determined by the charge on each carrier particle and depends therefore on the coating protein. The range of the interaction can be estimated from the Debye shielding length which is inversely proportional to the square root of the solution ionic strength. Finally, the third interaction is the specific antigen-antibody binding connected with the bridge formation between carrier particles. This bridge can only be formed when the coated particles are separated by not more than the length of the agglutinator molecule, this distance being henceforth termed the "bridgewidth".

If the coulomb repulsion is too weak, then the van der Waals attraction will cause nonspecific agglutination. On the other hand, if the coulomb repulsion is too strong, bridge formation will not occur, because the coulomb repulsion energy will be greater than the specific antigen-antibody bond energy. In order to maximize the sensitivity and specificity of the assay, it is desirable to adjust the magnitude and range of the coulomb repulsion so as to overcome the van der Waals attraction at short ranges less than a bridgewidth; while simultaneously making the coulomb interaction energy, at the longer range distance of a bridgewidth, small compared to the antigen-antibody bond energy.

The following is a detailed discussion of the bases for the conclusions that form the bases of this invention as set forth above. It is convenient to analyze the aggregation process which results from crosslinking of antibody-coated particles by antigen. However, the same analysis applies to the converse situation in which antibody is used to crosslink antigen coated spheres. As a first approximation, the aggregation process may be analyzed by considering only the formation of dimers from two particles, neglecting the formation of higher order polymers. Despite the apparently restrictive nature of this assumption, it provides considerable insight into the aggregation process even when the effect of higher order polymers is included. We seek to calculate the concentration of latex sphere dimers as a function of the total antigen concentrations $[ag]_t$ for arbitrary concentrations $[lp]_t$ of latex particles. The process of aggregation can be conceptually divided into two steps. In the first step each antibody-coated sphere is to be fixed in place in the solution. To this solution we now add $[ag]_t$ moles/l of antigen. The antigen becomes distributed between the solution and the antibody sites on the spheres. The relative proportion of bound and free antigen can be described using a law of mass action equation. The second step in the monomer-dimer reaction is the formation of antigen bridges between two spheres. In this step, we allow the spheres to depart from their fixed positions to form dimers. Again the dimerization reaction can be characterized using a law of mass action equation. This approach is valid because the processes involved are equilibrium processes and thus the final polymer distribution is independent of the thermodynamic path used to achieve it. We now describe quantitatively the two steps involved.

First, we consider the distribution of antigen between the solution and the spheres (antigens on the spheres are the ones responsible for the aggregation in step 2). n denotes the number of active antibody sites on each sphere. Also, we denote by $n_A$ the number of antigens bound to a single sphere. At equilibrium there will be $(n-n_A)$ unoccupied active antibody sites on elach sphere and [ag] moles/l of antigen in the solution. The law of mass action equation connecting the antigen concentration in the solution with the bound antigen on one sphere is $$n_A = K_o(n - n_A)[ag]. \quad (1)$$

In this equation $K_o$ is the equilibrium constant describing the interaction of free antigen with the antibody coated onto the sphere surface. It is convenient to express ag in terms of the total antigen concentration $[ag]_t$ added initially to the solution. This may be done by using the conservation of mass condition for antigen, namely, $$[ag]_t = n_A[lp]_t + [ag] \quad (2)$$

where $[lp]_t$ is the total concentration of latex spheres in moles/l. On combining (2) and (1) to eliminate [ag], we obtain a quadratic equation for the number of antigen bound to each sphere as a function of the total antigen concentration and the total latex particle concentration, i.e.

$$n_A = K_o(n - n_A)([ag]_t - n_A[lp]_t). \quad (1a)$$

Having obtained the number of bridge forming elements present on each sphere, we now proceed to describe the second conceptual step in the aggregation process. We denote by A an antigen-antibody complex on a particle and by B an active antibody site available for antigen binding. The linkage between two spheres involves the interaction of an A site on one sphere with a B site on another sphere. If there were only one A site and one B site on each sphere, the law of mass action equation for the interaction of the two particles would take the form $$[lp_2] = K_1[lp_1]^2, \quad (3)$$

$K_1$ being the equilibrium constant describing the interaction of one A site on one latex sphere with one B site on another latex sphere in the dimerization reaction. $[lp_1]$ is the concentration of latex particle dimers and $[lp_2]$ the concentration of latex particle monomers. One expects $K_1$ to be substantially smaller than $K_0$ because due to steric hindrance it is more difficult to form an antigen-antibody bond in the second step than an antigen-antibody bond formed in the first step. More importantly, the coulomb repulsion of the latex particles among themselves can interfere with the antigen-antibody bond formation in the second step as will be discussed. Eq. (3) has to be modified because there are many binding sites on the two interacting latex particles. As there are $(n - n_A)$ B sites on one sphere which can interact with $n_A$ A sites on the other sphere, the probability for a bond formation increases $n_A(n - n_A)$ fold. $K_1$ in Eq. (3) has accordingly to be modified to $K_1(n - n_A)n_A$. Thus Eq. (3) becomes $$[lp_2] = K_1 n_A(n - n_A)[lp_1]^2 \quad (4)$$

This equation predicts that in the limits $n_A << n$ or $n_A \to n$ the number of dimers formed out of monomers is quite small. This corresponds physically to the states where bridges cannot be formed in either of the two limits $n_A << n$ (where few A sites exist for linkage) and $n_A = n$ (where few B sites are available for linkage). On the other hand, a maximum number of dimers is formed when $n_A = (n - n_A) = n/2$. The concentration of antigen at which this occurs is that for which the average diffusion coefficient $\bar{D}$ of the solution will be minimal. We proceed now to show that, in general, the maximal aggregation occurs for $n_A = (n - n_A) = n/2$, no matter whether dimers, trimers or any order polymers are formed. The formation of a particle polymer out of m monomers can be described in the following way: First, a monomer is added to a dimer to form a trimer, then another monomer is added to the trimer to form a quadrimer and so on. All these steps are subject to the law of mass action with binding constants $K^{i,1}$, characterizing the reaction $$lp_{i+1} \rightleftarrows lp_i + lp_1$$

These law of mass action equations have the form $$[lp_{i+1}] = K^{i,1}[lp_i][lp_1] \quad (5)$$

In the special case $i = 1$ (see Eq. 4) we have found the $K^{1,1} = 2K_1 n_A(n - n_A)$. It is obvious that any $K^{i,1}$ will be proportional to $n_A(n - n_A)$ since the interaction of two spheres, no matter whether they are bound in a complex or not, involves an A site on one sphere and a B site on the other, and the affinity of the two spheres is dependent on how many A and B sites are available for binding. However, the constant of proportionality is not $K_1$ as for the dimerization reaction. This stems from the fact that in the formation of trimers and higher order polymers the added monomer can form bonds with more than one latex particle of the complex. In addition, a complex having m latex particles in it has $m \cdot n_A$ A sites and m·(n−$n_A$) B sites; part of which are not accessible for steric reasons. If we use the recursion relation (5) to form a polymer out of m monomers, we obtain $$[lp_m] = K_1 K_2 \cdots K_{m-1}\{n_A(n-n_A)\}^{m-1}[lp_1]^m. \quad (6)$$

Thus, the condition most conducive to polymerization is: $n_A = (n-n_A) = n/2$. This important conclusion states that the maximum aggregation, corresponding to the minima of the agglutination curves, occurs where the number of A sites is equal to the number of B sites, and the antigen concentration needed for this to happen is the one which makes the average diffusion constant minimal. In the case $n_A = (n-n_A) = n/2$ equation (1a) becomes especially simple:

$$1 = K_o([ag]_{tmax} - n/2[lp]_t) \quad (1b)$$

Here $[ag]_{tmax}$ is the total antigen concentration which produces maximal agglutination, i.e. minimal $\bar{D}$. Solving this equation for $[ag]_{tmax}$ leads to $$[ag]_{tmax} = (1/K_o) + (n/2)[lp]_t \quad (7)$$

This equation predicts that the antigen concentration required to produce maximum aggregation (minimal D) is a linear function of the total particle concentration $[lp]_t$. In the example set forth below, n=700 and $K_o \simeq 10^{10}$ 1/mole, the value of n indicates that in the example set forth below that of the 16,000 sites coated on a single sphere about 5% remain functional. $K_o$ can be expected to be of the same order of magnitude as the conventionally defined antigen-antibody affinity constant since the equilibrium process which defines $K_o$ does not require the close approach of two particles. With these values for n and $K_o$, we are now in a position to discuss the theoretical sensitivity of the assay. This will help us to understand how the minimal detectable antigen concentration $[ag]_{tmin}$ depends on the total particle concentration and on the parameters n, $K_o$ and $K_1$.

We will now proceed to calculate $[ag]_{tmin}$. In the limit of low antigen concentration, particle monomers and dimers will predominate, and higher order polymers will be almost absent. To first approximation one is led, therefore, to neglect the influence of trimers, quadrimers, etc. and to just consider the dimerization reaction responsible for a decrease of the average diffusion constant $\bar{D}$ in the particle suspension. For the dimerization reaction we have found a quantitative description in Eq. (4). In the limit of low antigen concentration one expects $n_A$ to be much smaller than n. This permits us to approximate Eq. (4) by $$[lp_2] \simeq K_1 n_A n [lp_1]^2 \quad (4a)$$

Eq. (4a) is an implicit equation for $[ag]_t$ if we express $n_A$ in terms of $[ag]_t$, $[lp]_t$, n and $K_o$. This can be done with the help of Eq. (1a). By approximating $(n-n_A)$ by n as in Eq. (4a), one obtains a simplified equation for $n_A$:

$$n_A \simeq K_o([ag]_t - n_A[lp]_t). \quad (1c)$$

If we solve this equation for $n_A$, the result is $$n_A \simeq \frac{K_o n[ag]_t}{1 + K_o n[lp]_t}. \quad (8)$$

In the example set forth below, the concentration of latex spheres used in the experiments ranged from $5 \times 10^{-13}$ moles/l to $10^{-11}$ moles/l. For these concentrations the product $K_o n [lp]_t$ ranges from 3.5 to 70. Therefore, Eq. (8) can be approximated by $$n_A \simeq \frac{[ag]_t}{[lp]_t}. \quad (8a)$$

This equation expresses $n_A$ in terms of the experimentally known quantities $[ag]_t$ and $[lp]_t$ and is consistent with the fact that for sufficiently high latex particle concentration and at sufficiently low antigen concentration all the added antigen is bound to the surface of the spheres.

Eq. (8a) permits us to write the concentration of dimers $[lp_2]$ in the following form using Eq. (4a) and (8a)

$$Q = \frac{[lp_2]}{[lp_1]} = K_1 n [ag]_t \frac{[lp_1]}{[lp]_t} \quad (9)$$

Q is the ratio of the dimer to the monomer concentration. Since $[lp]_t = 2[lp_2] + [lp_1]$ we find that $[lp_1]/[lp]_t = 1/(1+2Q)$. We are interested in finding the minimal detectable $[ag]_{tmin}$. Solving Eq. (9) for $[ag]_t$ yields $$[ag]_t = Q(1 + 2Q) \frac{1}{nK_1} \quad (10)$$

To determine $[ag]_{tmin}$ one estimates the smallest value of Q which is experimentally detectable. For example, when quasi-elastic light scattering spectroscopy is used to determine the extent of the agglutination reaction, a 5% drop in $\bar{D}$ from the diffusion constant of the single carrier particle is detectable. This corresponds roughly to a change in the value of Q from zero to 1/6. For this value of Q the factor $Q(1+2Q)$ equals 2/9. This derivation depends on the fact that $n_A > 1$ (in the example set forth below, $n_A$ varied from 3 to 60), and that $K_o n[lp]_t >> 1$. Using Eq. (8a) these restrictions are equivalent to the conditions $$1/(nK_o) << [lp]_t < [ag]_t$$

In the above regime Eq. (10) predicts that the minimum detectable antigen concentration is independent of the latex particle concentration $[lp]_t$ and $K_o$, and inversely proportional to n and $K_1$. The experimental results confirm that $[ag]_{tmin}$ is independent of $[lp]_t$; in the example set forth below, the first drop in $\bar{D}$ occurs for all the measured latex particle concentrations at about 5ng/ml = $3.3 \times 10^{-11}$ moles/l. We may use this result and n=700 to estimate $K_1$ from Eq. (10). $K_1 \sim 10^7$ l/moles is about a factor of 1,000 smaller than $K_o$ for two reasons; for the formation of the first antigen-antibody bond the antigen is still completely free to orient itself, such that all its antigenic determinates are easily accessible. On the other hand, in the bridge-forming step involving $K_1$ the orientation of the antigen is fixed through its first bond. Second, coulomb repulsion between the two interacting spheres reduces $K_1$ further. The expression for $[ag]_{tmin}$ obtained in Eq. (10) emphasizes that the essential parameters determining the sensitivity are n and $K_1$. Both $K_1$ and n are amenable to optimization by changing physical parameters of the system. To increase the sensitivity, one should maximize n by packing as many active sites on one sphere as possible. Otherwise one could use larger carrier particles or could provide more efficient coating procedures. However, it is technically difficult to perform light scattering measurements rapidly when the particle size is greater than $0.5\mu$. $K_1$ can be varied by changing salt concentration and pH of the suspending medium as is discussed above. As stated above, one is permitted to choose quite freely the particle concentration without affecting the assay sensitivity. When using a fairly high concentration, e.g. 0.02mg/ml of $0.357\mu$ latex particles, the experimenter need not be very careful to eliminate dust or large aggregates of proteins in sera since essentially all of the light will be scattered from the latex particles.

With the present invention it is possible to optimize the specificity and sensitivity of an antigen-coated or antibody-coated particle regardless of the efficiency of the particle coating step. As stated above, more active sites on the particles can be effected by using larger particles. However, rapid light scattering measurements are most conveniently performed with particles of a size between about $0.01\mu$ and $0.5\mu$. Any particles normally employed in agglutination reactions can be employed herein including bacteria, red blood cells, latex, polystyrene, glass, sepharose, polyactylamide or the like. Even though the sensitivity of the process of this present invention is not markedly affected by the concentration of the coated particles in suspension, it is preferred to employ a relatively high concentration of particles when determining the extent of reaction by quasi-elastic light scattering since extreme care need not be taken to eliminate dust or large protein aggregates when conducting the light scattering analysis since essentially all of the light scattering is effected by the coated particles.

Representative suitable antigens or antibodies that can be coated on the carrier particles include human chorionic gonadotropin, human luteinizing hormone, insulin, parathyroid hormone, digoxin, barbituates, diphenylhydantoin, hepatitis associated antigen, carcinoembryonic antigen and their associated antibodies.

Representative suitable buffers used to fix the pH and adjust the ionic strength are sodium phosphate, potassium phosphate, Tris, sodium borate, glycine and the like. In addition, salts such as sodium chloride, potassium chloride and the like may be used to adjust the ionic strength; and acids and bases such as sodium hydroxide and hydrochloric acid may be used to adjust the pH.

The following example illustrates the present invention and is not intended to limit the same.

EXAMPLE I

Suspensions of uniform latex polystyrene spheres (diameter usually $0.357\mu$, obtained from Dow Chemical Company) were diluted in 0.015 M borate buffer. The suspension was then slowly added to a solution containing specifically purified goat antimouse IgA (4.7 mg active ab/ml, obtained from Gateway Company). This procedure is necessary to prevent aggregation of the spheres during the coating process. The final mixture contained 2.5 mg latex particles and 470 $\mu$g of goat antimouse IgA per ml of solution. The following procedure was adopted to remove excess antibodies that did not adhere to the latex particles. After incubation of the solution described above at 4° C. overnight, it was spun at 15,000 rpm for ten minutes. The supernatant was discarded and the pellet resuspended in buffer. This centrifugation and resuspension process was then repeated. The resulting antibody coated latex particle stock suspension proved to be stable for at least two months at this concentration at 4° C. This procedure may result in a monolayer coating of the latex particles with the antibody molecules. Optical density measurements of the supernatant permitted a determination that on one $0.357\mu$ carrier particle there are approximately 8,000 ab molecules absorbed. This value corresponds to an ab surface density of 0.5 $\mu$g ab per $cm^2$. Therefore, one might expect that each latex sphere carries $2\times 8,000 = 16,000$ active ab sites. However, the absorption process denatures or makes inaccessible many of the ab sites so that only a small fraction of them are still active. Subsequently analysis of the results shows that, in fact, about 700 ab sites remain active on each sphere.

In order to set up a quantitative assay, one requires, besides the sample sera, a standard and a control serum. The control was prepared by adsorbing normal Balb/c mouse serum on a goat-antimouse-IgA sepharose colum. The standard was obtained by adding a measured amount of specifically purified M 167 (mouse myeloma protein, IgA class) to the IgA free normal BAlb/c control serum, such that the undiluted standard serum would contain 11.4 mg/ml M 167.

The IgA concentration was determined in the following mouse strains: Balb/c, A/J, Ce/J, CD-1, F1 hybrid A/J $\times$ Balb/c all pooled; Balb/c M 167 myeloma serum pooled; and two A/J x Balb/c F1 hybrid individuals. The diluent in most of the experiments contained 0.15 M borate buffer at pH 8.5, 0.06 M NaCl in a 1:2,000 dilution of IgA absorbed Balb/c serum and was filtered through a $1\mu$ nuclepore filter. Just prior to an assay the diluent was used to dilute part of the latex stock to a concentration of 0.017 to 0.27 mg/ml and to prepare serial dilutions (successive dilution factor of 2) of the standard, the control and the sample sera. The latex particle suspension was then filtered through a $1\mu$ nuclepore filter, and 25 $\mu$l aliquots of the latex particle suspension were mixed with 25 $\mu$l aliquots of the serial dilutions. The mixtures were incubated for 3-5 hrs. at room temperature and finally $\overline{D}$ was measured utilizing 100 $\mu$l pipettes as scattering cells. The average diffusion constant $\overline{D}$ of the agglutinated latex particle suspension was determined in the following way. Maintaining the temperature of the scattering cell at 25° C., we performed light scattering spectroscopic measurements at a scattering angle of 90° using a 15 mW Helium-Neon Laser. The output of a doubly scaled autocorrelator with 16 data channels and 4 delayed channels was displayed on a large oscilloscope screen and the average diffusion constant $\overline{D}$ was determined by visually fitting a single exponential generated by an RC circuit to the data points. $\overline{D}$ was determined in our experiments by measuring the time-time correlation function rather than the spectrum of the scattered light. These two procedures are equivalent since the time-time correlation function is just the Fourier transform of the spectral power density.

Light scattered from a strongly polydisperse system has a temporal correlation function which deviates from a single exponential. The higher the degree of latex particle aggregation, the more pronounced is this deviation. Thus, the determination of $\overline{D}$ through a single exponential fit is most appropriate for moderate degrees of agglutination. In fact, the measurements of $\overline{D}$ were most reproducible when $\overline{D}$ was greater than two thirds of the diffusion constant of the unaggregated latex spheres ($\bar{D}_{monomer}$), although we were able to extend the measurements down to a value of $0.1 \times \bar{D}_{monomer}$.

To optimize the sensitivity of the assay, to eliminate nonspecific agglutination and to minimize the measurement time required a first set of experiments was performed. The stability of a latex particles suspension against nonspecific aggregation depends on the pH and the salt concentration of the suspending medium, as will be discussed below. We determined that the goat anti mouse IgA coated latex particles are only stable for pH≧8 in 0.06 M NaCl and 0.015 M borate buffer. In turn, at pH 8.5 and in 0.015 M borate buffer the coated latex particles are only stable for NaCl concentrations of ≦.08 M. Thus, for all further experiments the reaction solutions were chosen to contain 0.06 M NaCl and 0.015 M borate buffer at pH 8.5. In addition, further experiments showed that the sensitivity of the assay is not significantly influenced by the concentration of latex particles. Hence we were at liberty to choose a latex particle concentration large enough to expedite the diffusion constant measuring process.

The standard agglutination curve obtained shown as a solid line and the sample curves show a marked minimum in $\bar{D}$ as a function of the antigen concentration. $\bar{D}$ is equal to the diffusion constant of latex particle monomers for high and very low antigen concentrations ($>2.5\mu g/ml$ and $<5$ ng/ml). Since the concentration of antigen is known at each point of the standard agglutination curve, we determine from the curves that the lowest antigen concentration which still produces detectable agglutination is about 5 ng/ml in the studied system. The smallest volume on which the assay could be performed is about 1 $\mu l$. The assay is therefore able to detect about 5 picogram of mouse IgA which corresponds to about $2 \times 10^7$ molecules. Once a standard curve of $\bar{D}$ vs $\log_2(c/c_0)$ is established for a sample of known concentration $c_0$ of antigen, one may determine the unknown concentration of antigen, $c_u$, in any test sample. To do this one simply prepares a similar dilution curve, $\bar{D}$ vs $\log_2(c/c_u)$ for the test sample and measures the displacement of this curve from the standard. Of course, it is not necessary to prepare an entire dilution curve for the test sample but generally $\bar{D}$ should be measured for at least two dilutions of the test sample to yield unambiguous results. The results indicated represent the control (normal IgA absorbed Balb/c serum) and show that no agglutination occurred for all dilutions shown. In fact, we extended our measurements up to a dilution of 1:14 ($-\log (c/c) = 3.8$) and observed no change in $\bar{D}$. Thus the agglutination appears to be completely specific for mouse IgA.

The concentration sensitivity of the LIA is very high (5ng/ml of IgA). Moreover, since the LIA can be performed in such small volumes (1 $\mu l$), the absolute amount of material detectable (about 5 pg IgA) may be less than by any other technique. This suggests that in conjunction with a sample concentration procedure, the LIA may be used to measure lower levels of antigen than previously possible. However, in the application discussed here the full range of sensitivity was never needed, since the IgA concentrations in mice are fairly high (30-300 $\mu g/ml$). It should be emphasized that the largest mean aggregate size of the latex spheres (corresponding to approximately 10 agglutinated latex particles is much smaller than that required for macroscopic precipitation and is also much smaller than the aggregate size detectable by other techniques such as turbiditimetry. Furthermore, the assay is very quick, permitting the measurement of one test tube in 10 seconds to 1 minute. Finally, the small sample volumes involved reduce drastically the amount of ab and ag needed per test tube.

The reagents employed in this experiment were optimized as follows. First the pH of the solution was chosen as far from the isoelectric point of the coating protein as possible so as to maximize the sphere charge. The pH, however, was left within the range 6-9 since outside this domain the specific antibody-antigen binding is usually diminished. Next, the ionic strength is gradually increased, so as to shorten the range of the coulomb interaction, until nonspecific agglutination occurs. In our experiments we find that specific aggregation does not occur below 0.02 M NaCl, and that spontaneous, nonspecific aggregation occurs at 0.08 M NaCl. Experimentally one chooses the optimum salt concentration at a level just below that at which nonspecific agglutination occurs.

We claim:

1. The process for forming a composition comprising an aqueous suspension of antigen-coated or antibody-coated particles to maximize sensitivity for determining the concentration of the agglutinator for the composition which comprises
   (A) coating carrier particles with the antigen or antibody,
   (B) suspending the coated particles in a liquid having a pH as far as possible from the isoelectric point of the particle coating without significantly reducing the binding capacity of the coating, to maximize particle charge,
   (C) increasing the ionic strength of the composition obtained by (B) to reduce the range of coulomb interaction until nonspecific agglutination occurs and
   (D) reducing the ionic strength of the composition by (C) to just below that where nonspecific agglutination occurs so that coulomb effect and the van der Waals forces on and exerted by the particles are balanced to effect determination of a minimum concentration of the agglutinator.

2. The process of claim 1 wherein the average size of the particles is between about 0.05 $\mu m$ M and 5 $\mu m$ M.

3. The process of claim 1 wherein the concentration of said particles is between about 1 $\mu g/ml$ and 500 $\mu g/ml$.

4. The process of claim 1 wherein the particles are polystyrene particles.

5. The process of claim 2 wherein the particles are polystyrene particles.

6. The process of claim 3 wherein the particles are polystyrene particles.

* * * * *